US006613923B1

(12) United States Patent
Bullock et al.

(10) Patent No.: US 6,613,923 B1
(45) Date of Patent: Sep. 2, 2003

(54) CATALYTIC IONIC HYDROGENATION OF KETONES USING TUNGSTEN OR MOLYBDENUM CATALYSTS WITH INCREASED LIFETIMES

(75) Inventors: R. Morris Bullock, Wading River, NY (US); Barbara F. M. Kimmich, Corpus Christi, TX (US); Paul J. Fagan, Wilmington, DE (US); Elisabeth Hauptman, Wilmington, DE (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 09/552,212

(22) Filed: Apr. 19, 2000

Related U.S. Application Data (63) Continuation-in-part of application No. 09/235,207, filed on Jan. 22, 1999, now Pat. No. 6,124,509.

(51) Int. Cl.$^7$ .............................. C07F 11/00; B01J 31/00
(52) U.S. Cl. .............................. 556/22; 556/23; 556/60; 502/155; 568/809; 568/814; 568/881
(58) Field of Search ............................ 556/22, 23, 60; 568/881, 809, 814; 502/155

(56) References Cited

U.S. PATENT DOCUMENTS

| 4,940,819 A | 7/1990 | Kiel et al. ............. 568/318 |
| 4,967,031 A | 10/1990 | Bullock ............. 585/250 |
| 5,182,246 A | 1/1993 | Fuchikami et al. ......... 502/161 |
| 5,578,741 A | * 11/1996 | Frey et al. ............. 585/360 |
| 6,124,509 A | * 9/2000 | Vogues et al. ............. 568/881 |

OTHER PUBLICATIONS

Tatsumi T., Kizawa, K., Tominaga, H., "Homogeneous Transfer Hydrogenation of Kentones Catalyzed by Molybdenum Complexes," *Chemical Society of Japan*, Chemistry Letters 191–194 (1977).
Kitamura, M., Ohkuma, T., Inoue, S., Sayo, N., Kumobayashi, H., Akutagawa, S., Ohta, T., Takaya, H. Noyori, R., "Homogeneous Asymmetric Hydrogenation of Functionalized Ketones," *J. Am. Chem. Soc.*, 110:629–631 (1988).
Ohkuma, T., Ooka, H., Hashiguchi, S., Ikariya, T., Noyori, R., "Practical Enantioselective Hydrogenation of Aromatic Ketones," *J. Am. Chem. Soc.*, 117:2675–2676 (1995).
Fujii, A., Hashiguchi, S., Uematsu, N., Ikariya, T. Noyori, R., "Ruthenium(II)–Catalyzed Asymmetric Transfer Hydrogenation of Ketones Using a Formic Acid–Triethylamine Mixture," *J. Am. Chem. Soc.*, 118:2521–2522 (1996).
Zhang, X., Taketomi, T., Yoshizumi, T., Kumobayashi, H., Akutagawa, S., Mashima, K., Takaya, H., "Asymmetric Hydrogenation of Cycloalkanones Catalyzed by BINAP–Ir(I)–Aminophosphine Systems," *J. Am. Chem. Soc.*, 115:3318–3319 (1993).
Ohkuma, T., Ooka, H., Ikariya, T., Noyori, R., "Preferential Hydrogenation of Aldehydes and Ketones," *J. Am. Chem. Soc.*, 117:10417–10418 (1995).
Shohei, H., Fujii, A., Takehara, J., Ikariya, T., Noyori, R., "Asymmetric Transfer Hydrogenation of Aromatic Ketones Catalyzed by Chiral Ruthenium(II) Complexes," *J. Am. Chem. Soc.*, 117:7562–7563 (1995).
Mizushima, E., Yamaguchi, M., Yamagishi, T., "Effective Catalysts for Transfer Hydrogenation of Ketones and Imines by Propan–2–ol: Ruthenium–Hydride or Ruthenium–Dihydride Complexes," *The Chemical Society of Japan*, Chemistry Letters 1997, 237 (1997).
Tooley, P.A., Ovalles, C., Kao, S.C., Darensbourg, D.J., Darensbourg, M.Y., "Anionic Group 6 Hydrides and Carboxylates as Homogeneous Catalysts for Reduction of Aldehydes and Ketones," *J. Am. Chem. Soc.*, 108: 5465–5470 (1986).
Song, J–S., Szalda, D.J., Bullock, R.M., Lawrie, C.J.C., Rodkin, M.A., Norton, J.R., "Hydride Transfer by Hydrido Transition–Metal Complexes. Ionic Hydrogenation of Aldehydes and Ketones, and Structural Characterization of an Alcohol Complex," *Angewandte Chemie*, 31(9): 1233–1235 (1992).
Marko, L., Nagy–Magos, Z., "Homogeneous Hydrogenation of Ketones Using Chromium Hexacarbonyl as Catalyst Precursor in the Presence of Bases," *Journal of Organometallic Chemistry*, 285: 193–203 (1985).
Chalones, P.A., Esteruelas, M.A., Joó, F., Oro, L.A., "Homogeneous Hydrogenation," *Kluwer Academic Publishers*, 15: 28–29, 42–47, 80–83, 128–131, 162–169, 176–177, 180–181 (1994).
Fuchikami, T., Ubukata, Y., Tanaka, Y., "Group 6 Anionic $\mu$–Hydride Complexes [HM$_2$(CO)$_{10}$]–(M=Cr, Mo, W): New Catalysts for Hydrogenation and Hydrosilylation," *Tetrahedron Letters*, 32(9): 1199–1202 (1991).

* cited by examiner

*Primary Examiner*—Porfirio Nazario-Gonzalez
(74) *Attorney, Agent, or Firm*—Margaret C. Bogosian (57) ABSTRACT

The present invention is a process for the catalytic hydrogenation of ketones and aldehydes to alcohols at low temperatures and pressures using organometallic molybdenum and tungsten complexes and the catalyst used in the process. The reactants include a functional group which is selected from groups represented by the formulas R*(C=O)R' and R*(C=O)H, wherein R* and R' are selected from hydrogen or any alkyl or aryl group. The process includes reacting the organic compound in the presence of hydrogen and a catalyst to form a reaction mixture. The catalyst is prepared by reacting Ph$_3$C$^+$A$^-$ with a metal hydride. A$^-$ represents an anion and can be BF$_4^-$, PF$_6^-$, CF$_3$SO$_3^-$ or Bar'$_4^-$, wherein Ar'=3,5-bis(trifluoromethyl)phenyl. The metal hydride is represented by the formula: HM(CO)$_2$[$\eta^5$:$\eta^1$—C$_5$H$_4$(XH$_2$)$_n$PR$_2$] wherein M represents a molybdenum (Mo) atom or a tungsten (W) atom; X is a carbon atom, a silicon atom or a combination of carbon (C) and silicon (Si) atoms; n is any positive integer; R represents two hydrocarbon groups selected from H, an aryl group and an alkyl group, wherein both R groups can be the same or different. The metal hydride is reacted with Ph$_3$C$^+$A$^-$ either before reacting with the organic compound or in the reaction mixture.

9 Claims, 5 Drawing Sheets

CATALYTIC IONIC HYDROGENATION OF KETONES USING TUNGSTEN OR MOLYBDENUM CATALYSTS WITH INCREASED LIFETIMES

RELATED APPLICATION

The present application is a continuation-in-part application of copending application Ser. No. 09/235,207, filed on Jan. 22, 1999, now U.S. Pat. No. 6,124,509, in the name of Voges, et al. and titled CATALYTIC IONIC HYDROGENATION OF KETONES USING TUNGSTEN OR MOLYBDENUM ORGANOMETALLIC SPECIES. This application is incorporated by reference herein in its entirety.

GOVERNMENT RIGHTS IN THE INVENTION

This invention was made with Government support under Contract No. DE-AC02-98CH 10886, between the U.S. Department of Energy and Brookhaven Science Associates. The Government has certain rights in the invention.

BACKGROUND OF THE INVENTION

The present invention is a catalyst for the hydrogenation of unsaturated organic compounds and a process that uses the catalyst and can be carried out at low temperatures and pressures. More specifically, the invention relates to a process for the hydrogenation of ketones and aldehydes to alcohols using organometallic tungsten (W) and molybdenum (Mo) complexes as catalysts.

Hydrogenation reactions involve the addition of hydrogen to an organic compound whereby, for example, a ketone can be reduced to an alcohol. Prior art processes have generally required the presence of a heterogeneous catalyst with a solid phase of platinum, rhodium, palladium or nickel along with relatively high hydrogen pressure and elevated temperature.

Traditional homogeneous catalysts for hydrogenation of ketones or aldehydes use precious metals such as rhodium (Rh), iridium (Ir) or ruthenium (Ru), which are extremely expensive and, therefore, frequently uneconomical. In contrast, the catalysts of the present invention, which use either molybdenum (Mo) or tungsten (W), are much less expensive to prepare, and, thus, offer economic advantages.

SUMMARY OF THE INVENTION

The present invention provides a catalyst and a process that uses the catalyst for the homogeneous catalytic hydrogenation of ketones to alcohols with $H_2$ as the stoichiometric redundant and organometallic tungsten (W) and molybdenum (Mo) complexes as the catalysts.

The present invention is a catalyst and a process for the catalytic hydrogenation of an organic compound that contains at least one reducible functional group. The catalyst and the process are particularly well suited to the hydrogenation of ketones and aldehydes. The functional group is selected from groups represented by the formulas $R^*(C=O)R'$ and $R^*(C=O)H$, wherein $R^*$ and $R'$ are selected from hydrogen (H) or any alkyl or aryl group. $R^*$ and $R'$ can both be selected from H or from an alkyl group or from an aryl group, and can be the same or different.

The process includes reacting the organic compound in the presence of hydrogen and a catalyst to form a reaction mixture. The catalyst includes a metal hydride and is prepared by reacting $Ph_3C^+A^-$ with the metal hydride. $A^-$ represents an anion and can be $BF_4^-$, $PF_6^-$, $CF_3SO_3^-$ or $BAr'_4^-$, wherein $Ar'=3,5$-bis(trifluoromethyl)phenyl.

The metal hydride is represented by the formula:

$$HM(CO)_2[\eta^5:\eta^1-C_5H_4(XH_2)_nPR_2] \qquad (1)$$

wherein M represents a molybdenum (Mo) atom or a tungsten (W) atom; X is a carbon atom, a silicon atom or a combination of carbon (C) and silicon (Si) atoms; n is any positive integer, preferably between 1 and 6; R represents two hydrocarbon groups selected from H, an aryl group, an alkyl group or a combination thereof, the preferred hydrocarbon groups are a cyclohexyl group ($C_6H_{11}$), a methyl group ($CH_3$), a phenyl group ($C_6H_5$) and a tert-butyl ($^tBu$) system. Both R groups can be the same or different. The metal hydride is reacted with $$Ph_3C^+A^- \qquad (2)$$

either before reacting with the organic compound or in the reaction mixture.

In one embodiment, the catalyst is prepared by reacting the metal hydride with $Ph_3C^+A^-$ in the reaction mixture and the anion ($A^-$) is $BF_4^-$, $PF_6^-$, or $BAr'_4^-$, wherein $Ar'=3,5$-bis(trifluoromethyl)phenyl. In another embodiment, the catalyst is prepared by reacting the metal hydride with $Ph_3C^+A^-$ prior to reacting with the organic compound and the anion ($A^-$) is $CF_3SO_3^-$.

The catalysts have a bridge made up of a carbon group ($CR_2$), a silicon group ($SiR_2$) or a combination of carbon and silicon groups that connect the cyclopentadienyl ligand ($-C_5H_4$) to the phosphine ligand ($PR_2$) of the metal hydride. The carbon/silicon bridge connects the cyclopentadienyl ligand ($-C_5H_4$) to the phosphine ligand ($PR_2$) of the metal hydride.

The process is carried out in the presence of hydrogen at a pressure of from 0.5 atmosphere to 5,000 psi, preferably at a pressure of from 1 atmosphere to 100 psi, and at a temperature of from 0° C. to 100° C.

The molybdenum and tungsten catalyst complexes of the present invention provide significant cost advantages over prior art processes, which use expensive rhodium, iridium and ruthenium catalyst complexes. The less expensive catalysts of the present invention make it practical to hydrogenate organic compounds in commercial operations that previously had not been economically feasible.

Hydrogenation processes that are currently in use employ Mo and W (inexpensive metals) to hydrogenate ketones under mild conditions of temperature and pressure. However, a limitation encountered with these processes is the decomposition of the catalysts, due to dissociation of a phosphine ligand. The present invention provides catalysts with significantly higher lifetimes and increased thermal stability. Moreover, the homogeneous organometallic Mo and W complexes of the present invention provide an effective hydrogenation catalyst at a considerably reduced cost over the prior art catalysts that use Rh (rhodium), Ir (iridium) or Ru (ruthenium) complexes.

DETAILED DESCRIPTION OF THE PREFERRED EMBODIMENTS

The present invention can be used for a variety of hydrogenation reactions. As used herein, hydrogenation means the reaction of hydrogen with an organic compound, and encompasses processes that can also be called reduction, whereby a compound accepts electrons and hydrogen is added to a compound.

The present invention is a method for the preparation of a series of Mo and W organometallic complexes that serve as catalyst precursors for homogeneous hydrogenation of ketones. The catalytically active species are prepared by reaction of a metal hydride $HM(CO)_2[\eta^5:\eta^1-C_5H_4(XH_2)_2PR_2]$ (M=Mo, W; R=H, an aryl group, an alkyl group or a combination thereof, preferably Cy, Me, Ph, where $Cy=C_6H_{11}$, $Me=CH_3$ and $Ph=C_6H_5$) with $Ph_3C^+A^-$ ($A^-$= an anion) and X=C and/or Si. Anions ($A^-$) shown to be effective include $OTf^-$ ($OTf=CF_3SO_3$), $BAr'_4^-$ [Ar'=3,5-bis(trifluoromethyl)phenyl], $PF_6^-$ and $BF_4^-$. In the case of $A^-=OTf^-$, the complexes can be isolated prior to the hydrogenation reaction and have the formula $TfOM(CO)_2[\eta^5:\eta^1-C_5H_4(XH_2)_2PR_2]$. In the cases of $A^-=BAr'_4^-$, $PF_6^-$, and $BF_4^-$, the catalytically active species is generated in the reaction mixture. The reactions are conducted under $H_2$ with pressures from as low as 0.5 atmospheres and up to as high as 5,000 psi. Catalysis can occur at temperatures from 20° C. to 100° C. or higher.

The present invention uses Mo and W (relatively inexpensive metals) to hydrogenate ketones under mild conditions of temperature and pressure. In addition, a carbon bridge of two or three carbons connecting the cyclopentadienyl ligand to the phosphine ligand is incorporated in the structure to decrease the decomposition of the catalysts due to dissociation of a phosphine ligand. These new catalysts have significantly higher lifetimes and thermal stability compared to previous Mo and W catalysts, resulting in significantly improved turnover numbers.

The present invention provides a process for hydrogenating ketones and aldehydes to alcohols using organometallic molybdenum and tungsten complexes as the catalysts. Using the process of this invention, unsaturated organic compounds can be hydrogenated to give the corresponding saturated derivatives. Organic compounds which may be hydrogenated in accordance with the present invention include but are not limited to ketones and aldehydes. The hydrogenation of ketones and aldehydes involves the overall addition of two hydrogen atoms to the carbon-oxygen double bond to result in the formation of the corresponding alcohol.

CATALYSTS

The active organometallic catalyst for the present invention is prepared by using a hydride-abstracting agent to remove a hydride from a transition metal hydride. The transition metal hydride has the form: $HM(CO)_2[\eta^5:\eta^1-C_5H_4(XH_2)_nPR_2]$, wherein M represents a molybdenum (Mo) atom or a tungsten (W) atom; X is a carbon atom, a silicon atom or a combination of carbon (C) and silicon (Si) atoms; n is any positive integer, preferably between 1 and 6; R represents H, an aryl group, an alkyl group or a combination thereof, wherein the preferred two hydrocarbon groups are selected from a cyclohexyl group ($C_6H_{11}$), a methyl group ($CH_3$), a phenyl group ($C_6H_5$) and a tert-butyl ($^tBu$) system and both R groups can be the same or different.

The hydride abstracting agent can have the form: $Ph_3C^+A^-$, where $A^-$ is an anion. Anions ($A^-$) shown to be effective include $PF_6^-$, $BF_4^-$, $OTf^-$, where $OTf=CF_3SO_3$ and $BAr'_4^-$ (where Ar'=3,5-bis(trifluoromethyl)phenyl).

The active catalyst can be prepared prior to being mixed with the organic compound that is being hydrogenated, or it can be generated in the reaction mixture. When the catalyst is prepared in the reaction mixture, the metal hydride is mixed with the organic compound and $Ph_3C^+A^-$. The turnover rate (i.e., the number of moles of ketone hydrogenated per mole of catalyst per unit of time) depends on the metal, the phosphine, and the counterion employed.

The hydrogenation reaction can take place at relatively low pressures compared to previously known catalytic hydrogenation processes. The process of the present invention can be carried out over a wide range of hydrogen pressures. However, at hydrogen pressures below 1 atmosphere, the reaction rates are relatively slow and, therefore, hydrogen pressures at or above 1 atmosphere are preferred. Experiments have been carried out at hydrogen pressures as high as 65 atmospheres and the results show that pressures above 65 atmospheres can also be used. The preferred hydrogen pressure is about 4 atmospheres.

A typical reaction of the present invention for the hydrogenation of diethyl ketone (3-pentanone) to 3-pentanol (Et= $C_2H_5$) is shown in Equation 3.

(3)

For many of the reactions, the alcohol formed by the hydrogenation reaction undergoes further reaction and produces the corresponding ether and one equivalent of water, as shown below:

(4)

The reactions of the present invention are preferably carried out in a liquid phase, that is, reaction components are dissolved in an organic solvent. The preferred solvent is the ketone or aldehyde which is to be hydrogenated (i.e., no solvent is used other than the reactant itself). However, any solvent which is chemically inert, which does not interfere with the hydrogenation reaction and which at least partially dissolves the catalyst may be employed. The solvents may be paraffinic, preferably having 5 through 20 carbons such as pentane, heptane, octane, etc. $C_6$ through $C_{12}$ aromatics such as toluene, xylene, mesitylene and benzene, or halogenated aromatic solvents, such as chlorobenzene, dichlorobenzene, fluorobenzene and trifluorotoluene, can also be used. Preferred solvents are dichloromethane (methylene chloride, $CH_2Cl_2$) and toluene ($C_6H_5CH_3$). If the reactants are mutually soluble, the use of a solvent is not necessary. In addition, the ketone or aldehyde can be partially soluble or it can be completely soluble in the solvent.

The hydrogenation process of the invention can be carried out over a wide range of temperatures, with the primary limiting factor being the freezing or boiling point of the solvent and reactants. A preferred temperature range is from about 0° C. to about 100° C., with a range of about 20° C. to about 30° C. most preferred for the sake of convenience.

The process can be carried out at ambient pressure and in any type of apparatus that enables intimate contact of the reactants and control of operating conditions. The hydrogenated product may be removed by known means such as distillation and chromatography.

Catalysts Having a Bridge Connecting the Cyclopentadienyl Ligand to the Phosphine Ligand The catalyst of the present invention overcomes the problems relating to the dissociation of the phosphine ligand in Mo and W catalysts. The structure of this catalyst system includes a bridge of one or more carbon or silicon groups or a combination of carbon and silicon groups, which connects the cyclopentadienyl ligand to the phosphine ligand. The catalytically active species are prepared by reaction of a metal hydride $HM(CO)_2[\eta^5:\eta^1—C_5H_4(XH_2)_nPR_2]$ (M=Mo, W; R=H, an aryl group, an alkyl group or a combination thereof, Cy, Me and Ph being preferred, where $Cy=C_6H_{11}$, $Me=CH_3$ and $Ph=C_6H_5$) with $Ph_3C^+A^-$ ($A^-$= an anion); X=C and/or Si; and n is any positive integer, preferably between 1 and 6. Anions ($A^-$) shown to be effective include $OTf^-$ ($OTf=CF_3SO_3$), $BAr'_4^-$[Ar'=3,5-bis (trifluoromethyl)phenyl)], $PF_6^-$ and $BF_4^-$.

Synthesis and Characterization of $C_2$-Ligands and $C_3$-Ligands

The phosphine ligands, $Li[\eta^5—C_5H_4(CH_2)_2PR_2]$ (shown as analogs 2–4 in Scheme 1, R=Ph, Cy, $^tBu$), were formed by reaction of spirodiene (shown in Scheme 1 as compound 1) with the appropriate lithium phosphide according to preparation methods disclosed by Kauffmann et al. (*Angew. Chem., Int. Ed. Engl.* 1980, 19, 328–29) and Kettenbach et al. (*Chem. Ber.* 1993, 126, 1657–1669). Both of these references are incorporated herein by reference in their entirety. While the $C_2$-ligands, $Li[C_5H_4(CH_2)_2PR_2]$, can be cleanly prepared as colorless to pale yellow powders via the spirodiene (1), the analogous $C_3$-ligand, $Li[C_5H_4(CH_2)_3PR_2]$, must be prepared via a longer route starting from $Cl(CH_2)_3PR_2$ using the Kettenbach method shown in Scheme 1.

Scheme 1

Consistent with Kettenbach's results, the $C_2$-ligands are formed in relatively high yields (>72%) and purity (>95%), while the $C_3$-alkylphosphine ligands are formed in only moderate yields (about 20–50%) and lower purity (about 60–80%). All purities were measured by $^1H$ and $^{31}P$ NMR. Specifically, Kettenbach found that the $C_3$—$PPh_2$ (5) analog was formed in 95% purity (51% yield), but the $C_3$—$P^iPr_2$ (isopropyl) analog was formed as an ochre powder in only 89% purity (65% yield). Similarly, the $C_3$—$PR_2$ analogs 6 and 7 were formed as yellow to light brown solids in purities of 80% and 57% respectively by NMR.

The previously unknown ligands $Li[C_5H_4(CH_2)_2PCy_2]$ (3), $Li[\eta^5—C_5H_4(CH_2)_3PCy_2]$ (6), and $Li[\eta^5—C_5H_4(CH_2)_3P^tBu_2]$ (7) were found to have $^{31}P$ and $^1H$ NMR data similar to those of the published ligands listed in Table I. The $^{31}P$ NMR resonances of the $C_3$-ligands are consistently shifted about 2 ppm downfield compared to the $C_2$-ligands. The $^1H$ NMR of the $C_3$-complexes is for the most part similar to the $C_2$ analogs. However, $LiC_5H_4(CH_2)_3PCy_2$ (6) shows a single $CH_2$ peak substantially upfield (δ−1.44 ppm).

TABLE I

| | Lithium[ω-Phosphanyl)alkyl]cyclopentadienes | | | |
|---|---|---|---|---|
| Complex | % purity by $^{31}P$ NMR | $^{31}P\{^1H\}$ NMR in THF (ppm) | $^1H$ NMR: $CH_2$ region (2H unless otherwise noted) | $^1H$ NMR: Cp region |
| $LiC_5H_4(CH_2)_2PPh_2$ (2) | 95+ | −15.1 | 2.35 (m), 2.60 (m) | 5.55 (m) |
| $LiC_5H_4(CH_2)_3PPh_2$ (5) | 80‡ | −13.8 | 1.64 (m), 2.08 (m), 2.60 (m) | 5.49 (m) 5.53 (m) |
| $LiC_5H_4(CH_2)_2PCy_2$ (3) | 95+ | −6.5 | 1.82 (m), 2.62 (m) | 5.49,(m) 5.55 (m) |
| $LiC_5H_4(CH_2)_3PCy_2$ (6) | 73‡ | −3.2 | −1.44 (m, 1H), 0.48 (m, 1H), 0.55 (m), 2.19 (m) | 5.17 (m) |
| $LiC_5H_4(CH_2)_2P^tBu_2$ (4) | 95+ | 27.1 | 1.70 (m), 2.67 (m) | 5.52 (m) 5.55 (m) |
| $LiC_5H_4(CH_2)_3P^tBu_2$ (7) | 57‡ | 30.6 | Assignment uncertan | 5.52 (m) |

TABLE I-continued

Lithium[(ω-Phosphanyl)alkyl]cyclopentadienes

| Complex | % purity by $^{31}$P NMR | $^{31}$P{$^1$H} NMR in THF (ppm) | $^1$H NMR : CH$_2$region (2H unless otherwise noted) | $^1$H NMR: Cp region |
|---|---|---|---|---|

‡estimated from $^{31}$P NMR of reactions with Mo(CO)$_3$ (diglyme) since impurities in LiC$_5$H$_4$(CH$_2$)$_3$PR$_2$ overlap with desired product.

Synthesis and Characterization of HMo(CO)$_2$[η$^5$—C$_5$H$_4$(CH$_2$)$_2$PR$_2$]

The reaction of Mo(CO)$_3$(diglyme) with Li[C$_5$H$_4$(CH$_2$)$_2$PR$_2$] (R=Ph, Cy, and $^t$Bu) at room temperature formed the anionic intermediates, Li{Mo(CO)$_3$[η$^5$—C$_5$H$_4$(CH$_2$)$_2$PR$_2$]} (shown in Scheme 2 as complexes 8–10), in high yields (about 90% by NMR). The highly air-sensitive tricarbonyl anions were identified by their characteristic IR bands (Table II). The five band υ(CO) IR spectra observed for lithium salts of CpMo(CO)$_3$$^-$ in THF is a function of the solvent separated ion pairing ability of Li$^+$. The related Na$^+$ and K$^+$ salts of CpMo(CO)$_3$$^-$ give only three bands, corresponding to the contact ion pairs. The lithium salts exist as a mixture of contact and solvent-separated ion pairs, leading to two additional bands observed. The IR of the simple LiCpMo(CO)$_3$ in THF (υ(CO)=1907, 1900 (sh), 1808, 1783 (m) and 1717 cm$^{-1}$) closely matches the IR spectra of complexes 8–10 shown in Table II.

Scheme 2

8 R = Ph
9 R = Cy
10 R = $^t$Bu

11 R = Ph
12 R = Cy
13 R = $^t$Bu

The $^{31}$P and $^1$H NMR of the lithium salts Li[η$^5$—C$_5$H$_4$(CH$_2$)$_3$PR$_2$] are also consistent with the formation of complexes 8–10. The $^{31}$P NMR resonances of Li[η$^5$—C$_5$H$_4$(CH$_2$)$_3$PR$_2$] shift only slightly upfield (<2 ppm) from the starting ligands 2–4. This supports the formation of "dangling phosphine" complexes (see Tables I and II). Formation of the phosphine-bound anions, Li[Mo(CO)$_2$[η$^5$:η$^1$—C$_5$H$_4$(CH$_2$)$_2$PR$_2$], are not observed for the Mo anions, based on the absence of $^{31}$P resonances downfield.

TABLE II

Li{M(CO)$_3$[η$^5$-C$_5$H$_4$(CH$_2$)$_n$PR$_2$]} complexes; NMR and IR data in THF

| M | R | n | | IR, υ(CO), cm$^{-1}$ | $^{31}$P NMR (ppm) | $^1$H NMR, ppm | | |
|---|---|---|---|---|---|---|---|---|
| | | | | | | C$_5$H$_4$(m) | CH$_2$'s | PR$_2$ |
| Mo | Ph | 2 | 8 | 1903, 1906 (sh), 1804, 1784 (m), 1715 | −13.2 | 4.89 (m), 5.01 (m) | 2.34 (m) | 7.26–7.44 (m) |
| Mo | Ph | 3 | 23 | 1902, 1892 (sh), 1804, 1779 (m), 1717 | −14.4 | 4.89 (m), 4.95 (m) | 1.73 (m), 2.07 (m), 2.44 (m) | 7.04–7.40 (m) |
| Mo | Cy | 2 | 9 | 1902, 1890 (sh), 1805, 1779 (m), 1714 | −1.8 | 4.87 (m), 4.98 (m) | Overlap w/Cy | 1.17–2.77 (m) |
| Mo | Cy | 3 | 24 | 1902, 1895 (sh), 1804, 1780 (m), 1715 | −3.9 | 4.87 (m), 4.95 (m) | 0.87 (m), ovlp w/ Cy, 2.34 (m) | 1.22–1.73 (m) |
| Mo | $^t$Bu | 2 | 10 | 1902, 1890 (sh), 1807, 1780 (m), 1715 | 31.8 | 4.88 (m), 5.02 (m) | 1.63 (m), 2.43 (m) | 1.12(d,$^3$J$_{PH}$ = 10.5 Hz) |
| Mo | $^t$Bu | 3 | 25 | 1902, 1890 (sh), 1803, 1779 (m), 1715 | 29.8 | 4.89 (m), 4.98 (m) | 0.89 (m), 1.71 (m),2.40(m) | 1.10(d,$^3$J$_{PH}$ = 10.4 Hz) |
| W | Ph | 2 | 14 | 1926, 1897, 1799, 1715 | −13.3 | assign uncertain | assignts uncertain | assignts uncertain |
| W | Cy | 2 | 15 | 1897, 1885 (sh), 1800, 1778 (m), 1713 | −1.9 | 4.91 (m), 5.02 (m) | assignts uncertain | assignts uncertain |

TABLE II-continued

Li{M(CO)$_3$[η$^5$-C$_5$H$_4$(CH$_2$)$_n$PR$_2$]} complexes; NMR and IR data in THF

| M | R | n | IR, ν(CO), cm$^{-1}$ | $^{31}$P NMR (ppm) | C$_5$H$_4$(m) | $^1$H NMR, ppm CH$_2$'s | PR$_2$ |
|---|---|---|---|---|---|---|---|
| W | $^t$Bu | 2 | 16 1896, 1885 (sh), 1800, 1776 (m), 1714 | 28.6 | 4.92 (m), 5.05 (m) | 1.63 (m), 2.48 (m) | 1.11(d, $^3$J$_{PH}$ = 13.9 Hz) |

Addition of an excess (1.1 to 1.3 equivalents) of acetic acid to complexes 8–10 led to the formation of the hydride complexes, trans-HMo(CO)$_2$[η$^5$:η$^1$—C$_5$H$_4$(CH$_2$)$_2$PR$_2$] (11–13, R=Ph, Cy, $^t$Bu), which were isolated in 30–72% nonoptimized yields (Scheme 2, Table III). The yield for the phenyl complex (8) was lower compared to the alkyl-substituted complexes (about 30% vs. about 50–72% for complexes 9–10). While small amounts of additional hydride species were observed by $^1$H NMR during the reaction, the presence of the cis isomers could not be confirmed. This route was significantly cleaner and gave higher yields than that starting from Mo(CO)$_3$(NCMe)$_3$ (yields <35%). The trans-hydrides are pale yellow air-sensitive crystalline solids, which are easily soluble in CH$_2$Cl$_2$ and toluene and can be purified by recrystallization from solvent mixtures such as toluene/pentane or CH$_2$Cl$_2$/hexane. The hydrides appear to be quite stable in solution, showing only minor signs (<5%) of decomposition after many days in CD$_2$Cl$_2$ at room temperature under argon.

The hydrides 11–13 were characterized by a series of NMR experiments. The chemical shifts of the $^{31}$P NMR for hydrides 11–13 were found at 74.4, 80.6, and 103.8 ppm respectively. Coordination of the phosphine to the metal is accompanied by a downfield shift of about 100 ppm from the resonance of the "dangling phosphine" intermediates 8–10 (Table II and III). The phosphorous peaks are quite broad with w$_{1/2}$=about 30 Hz for complexes 11 and 13, while w$_{1/2}$=about 200 Hz for complex 12. This phenomenon was also observed for the simple non-bridged analogs, CpMoH(CO)$_2$(PPh$_3$) and CpMoH(CO)$_2$(PCy$_3$) (Table III) and is due to room temperature trans to cis isomerization. When the $^{31}$P NMR of complex 12 is taken at −89° C. the peak the broad resonance at δ 80.6 (w$_{1/2}$≈200 Hz) sharpens to give two sharp peaks (w$_{1/2}$=about 7 Hz) at δ 78.7 (97.7%) and 89.3 (2.3%). This is strong evidence that complex 12 (and the other hydrides by analogy) are isomerizing at room temperature. The shifts of the C$_0$—PPh$_3$ and C$_0$—PCy$_3$ species (72.2 and 76.2 ppm respectively) are similar to the related C$_2$-bridged species, C$_2$—PPh$_2$ and C$_2$—PCy$_2$. Variations in the chemical shift of the $^{31}$P of complexes 11–13 are governed by steric and electronic factors. According to the work done by B. E. Mann (Adv. Organomet. Chem., 1974,

TABLE III

IR and Selected NMR Data for HM(CO)$_2$[η$^5$:η$^1$-C$_5$H$_4$(CH$_2$)$_n$PR$_2$] where M = Mo or W, R = Ph, Cy, or $^t$Bu and n = 2 or 3

| Complex | | IR, ν(CO), cm$^{-1}$ in THF | $^{31}$P{$^1$H} NMR in CD$_2$Cl$_2$ | $^1$H NMR (ppm), in CD$_2$Cl$_2$ M-H (J, Hz) | CH$_2$'s (J, Hz) |
|---|---|---|---|---|---|
| HMo(CO)$_2$Cp(PPh$_3$) | | 1939 (s), 1864 (s) | 72.2 (br) | −5.57 (br) | |
| trans-HMo(CO)$_2$Cp(PCy$_3$) | | 1927 (vs), 1850 (s) | 76.2 (br) | −6.96 (d, J$_{P-H}$ = 20.0) | |
| HMo(CO)$_2$[η$^5$:η$^1$-C$_5$H$_4$(CH$_2$)$_2$PPh$_2$] | 11 | 1939 (s), 1864 (vs) | 74.4 (br) | −5.25 (d, J$_{P-H}$ = 27.6) | 2.34 (d,t, J$_{P-H}$ = 28.1, 6.8), 3.00 ("q", J = 7.4) |
| HMo(CO)$_2$[η$^5$:η$^1$-C$_5$H$_4$(CH$_2$)$_2$PCy$_2$] | 12 | 1927 (s), 1848 (vs) | 80.6 (br) | −5.81 (d, J$_{P-H}$ = 26.8) | 2.38 (m), 2.47(m) |
| HMo(CO)$_2$[η$^5$:η$^1$-C$_5$H$_4$(CH$_2$)$_2$P$^t$Bu$_2$] | 13 | 1922 (s), 1845 (vs) | 103.8 (br) | −5.74 (d, J$_{P-H}$ = 24.6) | 2.34–2.51 (m) |
| HW(CO)$_3$[η$^5$:η$^1$-C$_5$H$_4$(CH$_2$)$_2$PPh$_2$]$^†$ | 17 | 2015 (s), 1923 (vs) | −14.1 (s) | −7.21 (br) | assign. uncertain |
| HW(CO)$_3$[η$^5$:η$^1$-C$_5$H$_4$(CH$_2$)$_2$PCy$_2$]$^†$ | 18 | 2015 (s), 1922 (vs) | −2.1 (s) | −7.21 (br) | Ovlp w/Cy's |
| HW(CO)$_3$[η$^5$:η$^1$-C$_5$H$_4$(CH$_2$)$_2$P$^t$Bu$_2$]$^†$ | 19 | 2015 (s), 1922 (vs) | 29.4 (s) | −7.21 (brd, JW-H = 37) | 1.60 (m), 2.58 (m) |
| HW(CO)$_2$Cp(PPh$_3$) | | 1932 (vs), 1854 (s) | 41.6 (brd, 281) | −6.88 (br) | |
| HW(CO)$_2$Cp(PCy$_3$) | | 1920 (vs), 1832 (s) | 43.7 (brd, 248) | −7.68 (brd) | |
| HW(CO)$_2$[η$^5$:η$^1$-C$_5$H$_4$(CH$_2$)$_2$PPh$_2$] | 20 | 1934 (s), 1856 (vs) | 43.0 (brd, 295) | −6.87 (brd, JP-H = 20.6) | 2.35 (dt, 27.2, 6.9), 3.07 (brm) |
| HW(CO)$_2$[η$^5$:η$^1$-C$_5$H$_4$(CH$_2$)$_2$PCy$_2$] | 21 | 1921 (s), 1840 (vs) | 47.9 (brd, 293) | −7.44 (brd, J$_{P-H}$ = 26.9) | ovlp w/Cy's |
| HW(CO)$_2$[η$^5$:η$^1$-C$_5$H$_4$(CH$_2$)$_2$P$^t$Bu$_2$] | 22 | 1917 (s), 1836 (vs) | 82.7 (vbr) | −7.29 (brd, J$_{P-H}$ = 27.1) | 2.43 (dt, 20.9, 7.1), 2.58 ("q", 7.2) |
| HMO(CO)$_3$[η$^5$:η$^1$-C$_5$H$_4$(CH$_2$)$_3$PPh$_2$] | 26 | 1936 (s), 1858 (vs) | 54.6 (br) | −5.95 (d, J$_{P-H}$ = 33.9) | 1.60 (dm, 24.4), 2.20 (m), 2.49 (m) |
| HMo(CO)$_3$[η$^5$:η$^1$-C$_5$H$_4$(CH$_2$)$_3$PCy$_2$]$^†$ | 27 | — | 68.7 (br) | −6.63 (d, J$_{P-H}$ = 52.8) | 0.89 (m), ovlp w/Cy, 2.17 (m) |
| HMo(CO)$_3$[η$^5$:η$^1$-C$_5$H$_4$(CH$_2$)$_3$P$^t$Bu$_2$]$^†$ | 28 | — | 90.7 ? | −6.16 (d, J$_{P-H}$ = 70.3) | assign. uncertain |

$^†$Complexes formed in situ; all NMR data in THF.

12, 135–213, which is incorporated herein in its entirety), as the steric demand of the substituent increases (Ph<Cy<$^t$Bu), the bond angle (M—P—C) also increases, leading to increased shielding of the phosphorous atom as can be seen from the data in Table III.

Hydrogenations of 10 Eguiv. Pentanone in $CD_2Cl_2$ Under Less than 4 atm $H_2$

Nonbridged complexes, such as [CpM(CO)$_2$PR$_3$(3-pentanone)]BAr'$_4$ (M=Mo, W; R=Ph, Cy, Me), can hydrogenate ketones such as 3-pentanone at room temperature and under less than 4 atm $H_2$. While these catalysts are useful, they are slow and tend to decompose under the reaction conditions. Thermally more stable and active catalysts are provided by the present invention by tethering the phosphine to the cyclopentadienyl group.

The reactivity of the chelated phosphine complexes HM(CO)$_2$C$_5$H$_4$(CH$_2$)$_n$PR$_2$(n=2, M=Mo or W; R=Ph, Cy, or $^t$Bu, and n=3, M=Mo, R=Ph), 11–13 and 20–22 and 26–28, differs significantly from that of the nonbridged species CpM(CO)$_2$PR$_3$H (M=Mo, W; R=Ph, Cy, Me). This implies that the catalytic behaviors of these two classes of complexes may also vary. Preliminary results indicated that the reactivity of the W catalysts is generally much slower than their Mo analogs. Therefore, experiments were conducted using the Mo systems to minimize the run times. Because the ketone complexes [trans-Mo(CO)$_2$Cp(CH$_2$)$_2$PR$_2$(ketone)]$^+$BAr$_4$'$^-$ were not cleanly formed (i.e., other metal complexes in addition to the ketone complexes were formed), it is necessary to generate the catalyst in situ. The in situ catalysts formed by the abstraction of the hydride from HMo(CO)$_2$[$\eta^5$:$\eta^1$—C$_5$H$_4$(CH$_2$)$_2$PR$_2$] were studied under the same reaction conditions used for the nonbridging catalysts (note that the Mo—C$_0$—PCy$_3$ catalysts were also generated in situ).

The reactions were run under initial reaction conditions of 30 mM catalyst (in situ), 300 mM 3-pentanone, less than 4 atm $H_2$ at room temperature (about 23° C.), using $CD_2Cl_2$ as the solvent. The catalytic solutions were not stirred, and the tubes were kept in the absence of light. The available headspace of the NMR tube allowed for about 1.5 mL of $H_2$ to be added. Even at about 3.8 atm, this meant that at most 11 molar equivalents of dihydrogen were present during the reaction. Additional $H_2$ was therefore added during the reactions as needed. The reactions were followed by $^1$H and $^{31}$P NMR. 3-Pentanol and its ether were observed growing in the $^1$H NMR. The ether was present as a minor byproduct and was usually present in less than 25%. Bibenzyl was used as an internal standard for the $^1$H NMR. Extensive overlap in many regions of the $^1$H NMR spectra made it difficult to obtain good integrations for turnover numbers.

Figure 1:
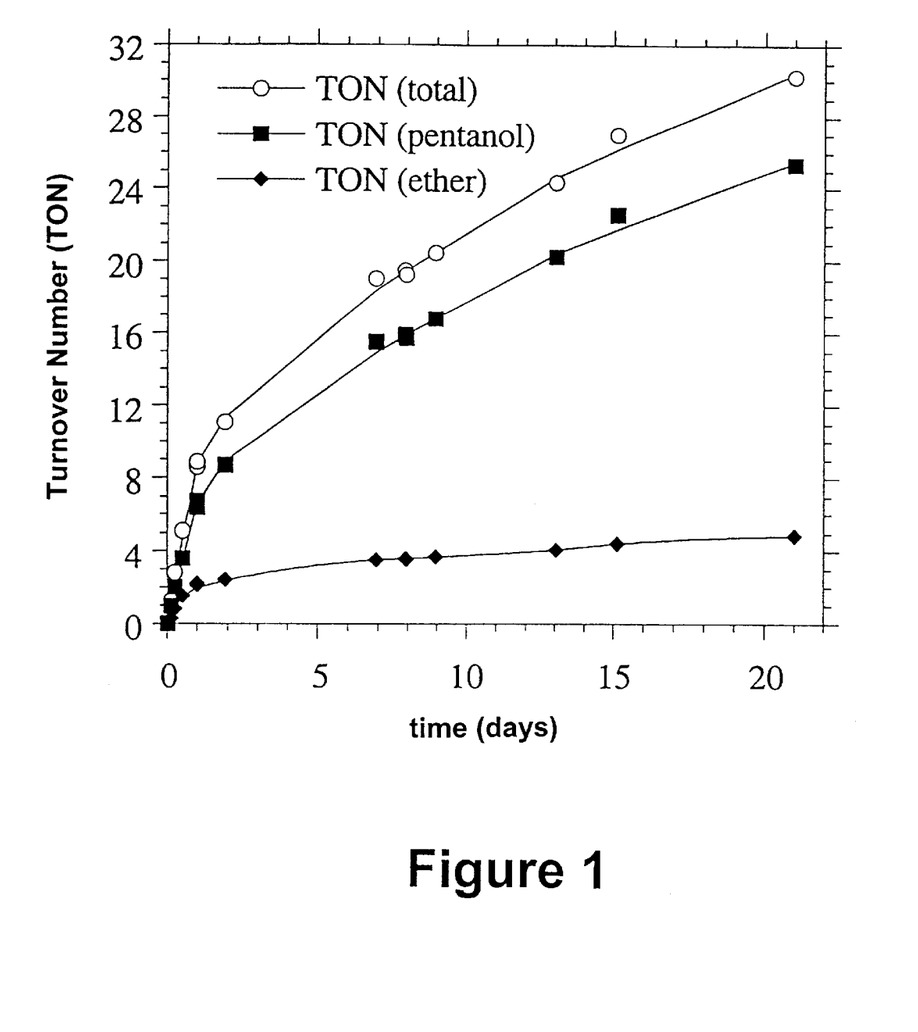
FIG. 1 shows a graph of total number of turnovers (TON) versus time for the hydrogenation of 3-pentanone (300 mM) by $HMo(CO)_2Cp(CH_2)_2PCy_2+Ph_3C^+B Ar'_4^-$.

FIG. 1 shows the hydrogenation of 3-pentanone (300 mM) by HMo(CO)$_2$C$_5$H$_4$(CH$_2$)$_2$PCy$_2$+Ph$_3$C$^+$BAr$_4$'$^-$ (both 30 mM) in $CD_2Cl_2$ under less than 4.1 atm $H_2$. TON (total number of turnovers) refers to the concentration of the product (3-pentanol and its ether) present in solution as measured by the integration of the CH resonances of the $^1$H NMR. Once the ketone was mostly hydrogenated, 10 additional equivalents of 3-pentanone were added to the reaction solution along with about 3.8 atm of $H_2$. The results in FIG. 1 show that the catalyst slows down substantially after the first 10 turnovers. The addition of more 3-pentanone appears to often disturb the active catalyst, sometimes leading to catalyst death. In the test results shown in FIG. 1, the catalyst remains active, even after two additions of 3-pentanone.

Figure 2:
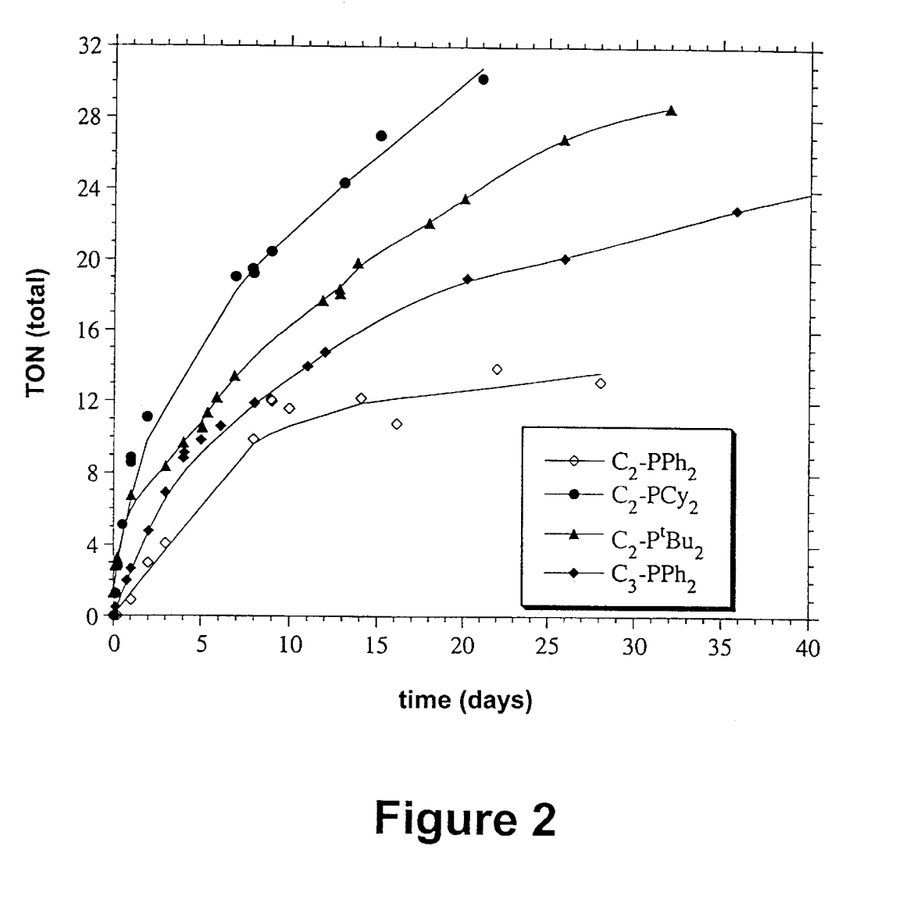
FIG. 2 shows a graph of total number of turnovers (TON) versus time for the ionic hydrogenation of 3-pentanone by a series of $C_2$- and $C_3$-bridged catalysts.

FIG. 2 shows the in situ ionic hydrogenation of 3-pentanone by a series of C$_2$- and C$_3$-bridged catalysts, generated in situ by reaction of HMo(CO)$_2$[$\eta^5$:$\eta^1$—C$_5$H$_4$(CH$_2$)$_2$PR$_2$] (R=Ph, Cy and $^t$Bu) and Ph$_3$C$^+$BAr$_4$'$^-$ in the presence of 3-pentanone. Initial reaction conditions were: 30 mM catalyst, 300 mM 3-pentanone, less than 4.1 atm $H_2$, $CD_2Cl_2$ and room temperature (about 23° C.). Additional 3-pentanone was sequentially added to the catalytic solution in 10 equiv. increments. Additional hydrogen was added as needed. FIG. 2 shows that the tethered phosphine Mo complexes are effective catalysts for the ionic hydrogenation of 3-pentanone, however, their catalytic rate is still quite slow under these conditions. Of the C$_2$-bridged catalysts, the cyclohexyl phosphine system forms the most active catalyst, followed by the tert-butyl and phenyl phosphine systems. This reactivity trend is not dissimilar to those of the unbridged C$_0$ system, where the cyclohexyl substituted phosphine catalyst was superior to its phenyl analog. It was observed that the C$_2$-bridged tert-butyl phosphine substituted phosphine was not as good a catalyst as its cyclohexyl analog. It is believed that the t-butyl groups are simply too sterically hindered to allow good phosphine binding to the metal. This is also reflected in the catalysts' poorer thermal stability. Notably, the C$_3$-bridged-PPh$_2$ system is substantially better than its C$_2$-bridged-PPh$_2$ analog under these reaction conditions.

Figure 3:
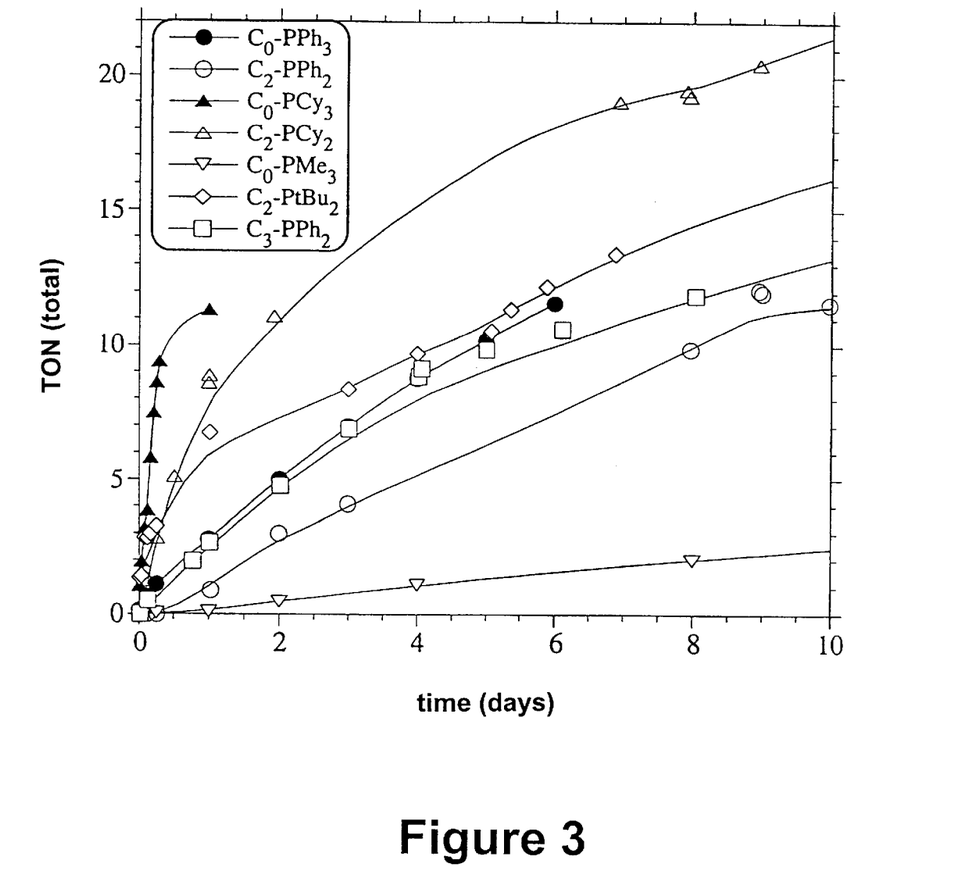
FIG. 3 shows a graph of total number of turnovers (TON) versus time for the ionic hydrogenation of 3-pentanone by a series of $C_2$-bridged and nonbridged ($C_0$) Mo catalysts.

FIG. 3 shows the ionic hydrogenation of 3-pentanone by a series of C$_2$-bridged and nonbridged (C$_0$) Mo catalysts. The initial reaction conditions were 30 mM catalyst, 300 mM 3-pentanone, 3 atm $H_2$, $CD_2Cl_2$ and 23° C. All bridged catalysts were formed in situ. Additional 3-pentanone was sequentially added to the catalytic solution in 10 equiv. increments. Of particular interest is the catalytic activity of the C$_3$—PPh$_2$ system. The results in FIG. 3 indicate that the activity of the C$_3$—PPh$_2$ system is approximately the same as the C$_0$—PPh$_3$ system under the chosen conditions. It is believed that the added flexibility of the C$_3$-bridge allows the C$_3$-bridged analogs to have similar activities to the nonbridged systems. This is in contrast to the C$_2$-system which is more constrained, leading to variation in the reactivity. The C$_3$—PPh$_2$ system continues to hydrogenate 3-pentanone, even after 20 turnovers.

When comparing the ionic hydrogenations using C$_2$-bridged systems to the nonbridged (C$_0$) catalysts, it appears that the nonbridged catalysts are more active (FIG. 3). Thus, the C$_0$—PCy$_3$ catalyst is more active than the C$_2$—PCy$_2$ catalyst. It is important to note, however, that at about 10 turnovers, the C$_0$—PCy$_3$ catalyst has decomposed. As a result, even though the bridged catalysts are initially slower under these conditions (FIG. 3), they are actually longer lived, and give higher TON numbers. The tethered phosphine catalysts (R=Cy and $^t$Bu) continue to hydrogenate 3-pentanone when it is sequentially added to the solution (FIG. 2). Results indicate that the C$_2$-bridged Mo—PCy$_2$ catalyst is substantially more stable than the related non-bridged analog. Notably, the $^{31}$P NMR spectra of the catalysis solutions exhibit only small changes after many days of catalysis. It is unclear why the C$_2$-bridged Mo—PPh$_2$ catalyst apparently dies after 10 turnovers (see FIG. 2). The $^{31}$P NMR of this system indicate that a an new complex becomes dominant in solution over time. However, it is possible that decomposition of the catalyst is brought on by the disruption of the catalytic system when additional 3-pentanone is added. In particular, the solutions are handled under argon, not under hydrogen, which could be negatively affecting the catalysis.

Figure 4:
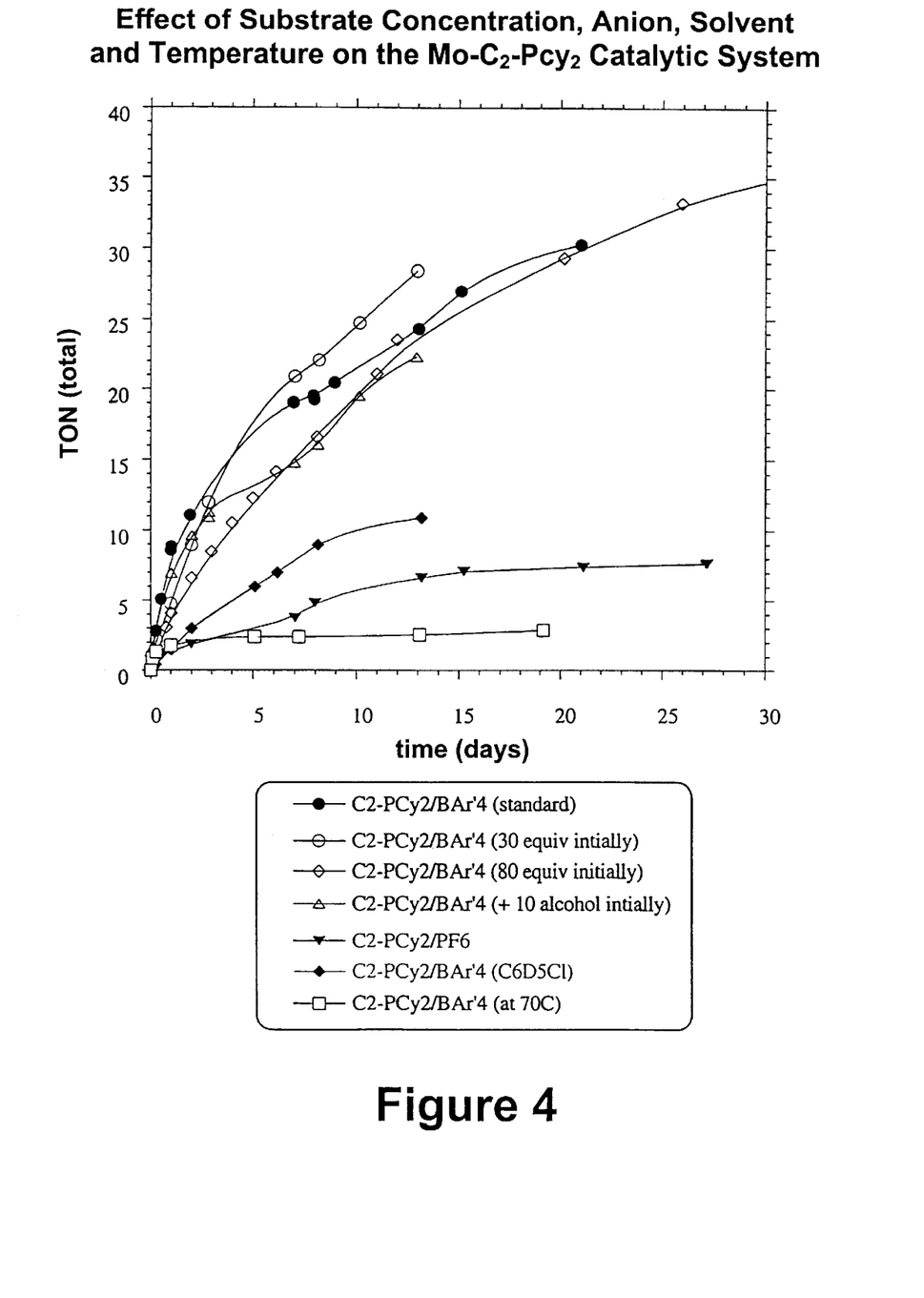
FIG. 4 shows a graph of total number of turnovers (TON) versus time for the ionic hydrogenation of 3-pentanone by $HMo(CO)_2Cp(CH_2)_2PCy_2+Ph_3C^+A^-$ ($A=BAr'_4$ or $PF_6$).

A number of experiments were conducted to study the product and substrate inhibition on the HMo(CO)$_2$Cp(CH$_2$)$_2$PCy$_2$/Ph$_3$C$^+$A$^-$ catalytic system. FIG. 4 shows the ionic hydrogenation of 3-pentanone by HMo(CO)$_2$Cp(CH$_2$)$_2$PCy$_2$+Ph$_3$C$^+$A$^-$ (A=BAr'$_4$ or PF$_6$). Initial reactions conditions were 30 mM catalyst, 300 mM 3-pentanone (10 equivalents), 4 atm H$_2$, and 23° C. All catalysts were formed in situ. Reactions were in CD$_2$Cl$_2$ at 23° C. unless otherwise indicated. Additional 3-pentanone was sequentially added to the catalytic solution in 10 equiv. increments.

The results in FIG. 4 indicate that the presence of 10 equivalents of 3-pentanol (product) at the beginning of the reaction does not significantly inhibit catalysis for the cyclohexyl-tethered complex. When 30 equivalents or even 80 equivalents of 3-pentanone are initially added to the reaction solution, initial catalysis rates are slower, but overall TON's are eventually the same or better than those reactions in which 3-pentanone is added in 10 equivalent portions. The results in FIG. 4 show that catalysis slows after about 10 equivalents. Again, it is important to note that only about 11 equivalents of H$_2$ are present at any given time for these reaction conditions. Thus, the above experiments are likely limited by lack of hydrogen. Nothing in the $^{31}$P NMR clearly indicates why the reaction is slowing. If the results are compared to the standard hydrogenation (10 equiv. 3-pentanone added sequentially) only small differences are observed in the rates (FIG. 4) and the $^{31}$P NMR's. The $^{31}$P NMR's of these reactions show that the major species (δ 74.6 ppm) in solution were the same in all cases, but the concentration of the minor species (δ 77.3, 77.0 and 76.6 ppm) differs somewhat for the runs.

Ionic Hydrogenation Under More Concentrated Conditions

A second set of reaction conditions for ionic hydrogenation were studied in order to minimize any interruption of the catalytic system. The reactions were run in a solution of 3-pentanone containing 10% benzene-d$_6$ as a lock solvent. These reactions were also run in Young NMR tubes (as were the CD$_2$Cl$_2$ reactions), allowing for the same type of NMR analysis discussed above. All other conditions, including catalyst concentration and H$_2$ pressure, were unchanged. The new reaction conditions avoided the use of halogenated solvents and eliminated the need to recharge the NMR tube with additional 3-pentanone. A major drawback to these conditions is that the reactions are now being run under a deficiency of H$_2$. Thus it was still necessary to frequently recharge the NMR tubes with dihydrogen.

Figure 5:
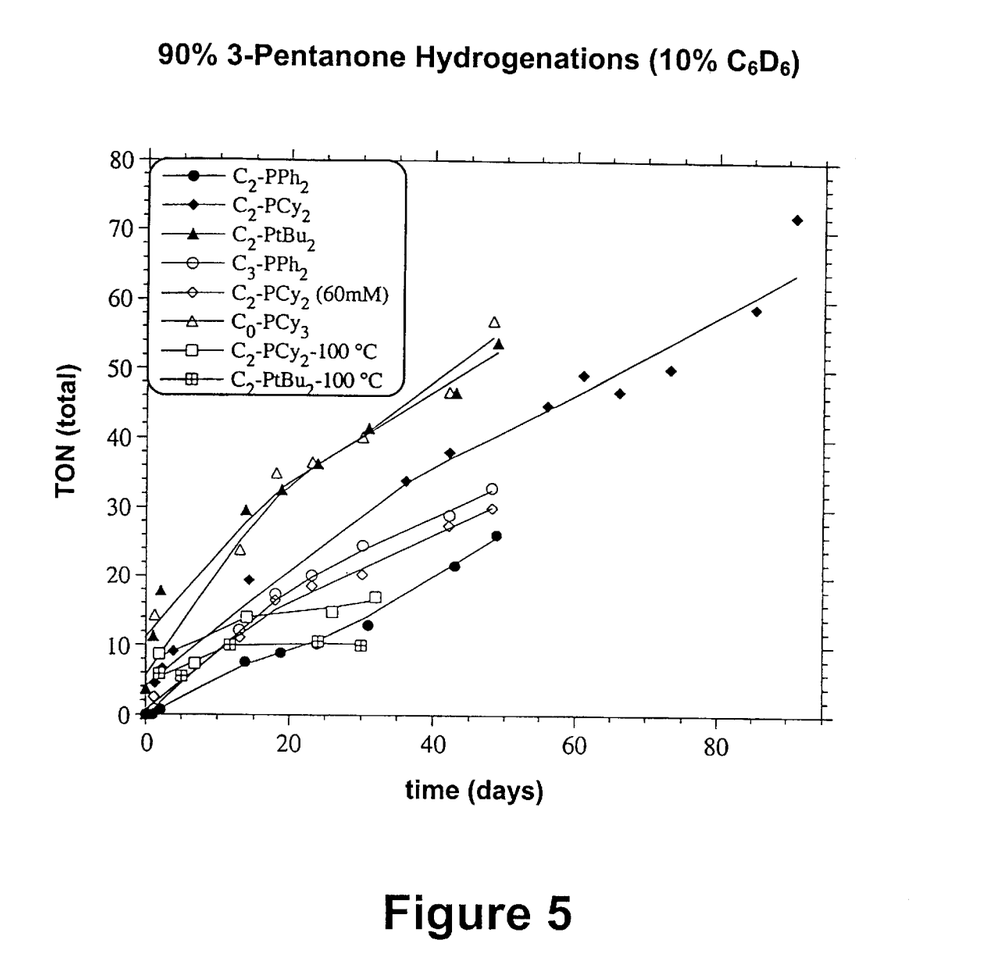
FIG. 5 shows a graph of total number of turnovers (TON) versus time for the ionic hydrogenation of 3-pentanone under "concentrated" conditions.

The results for the ionic hydrogenation of 3-pentanone under "concentrated" conditions are shown in FIG. 5. For these tests, the solutions contained 10% C$_6$D$_6$ by volume. 3-pentanone (8.91 M) was hydrogenated by HMo(CO)$_2$C$_5$H$_4$(CH$_2$)$_2$PCy$_2$+Ph$_3$C$^+$BAr'$_4$$^-$ (both 30 mM) in CD$_2$Cl$_2$ under less than 4.1 atm H$_2$. TON refers to the total concentration of product (3-pentanol and its ether) present in solution as measured by the integration of the CH resonances in the $^1$H NMR.

The results in FIG. 5 appear to be somewhat different than those for the dichloromethane reactions. The general trend for initial TON rates is as follows: C$_2$—P$^t$Bu$_2$>C$_0$—PCy$_3$>C$_2$—PCy$_2$>C$_3$—PPh$_2$>C$_2$—PPh$_2$. Notably, the C$_2$—PCy$_2$ system is somewhat slower under the concentrated conditions than under standard conditions. The C$_2$—P$^t$Bu$_2$ system is the most effective catalyst under the 90% pentanone conditions; in fact, the C$_2$—P$^t$Bu$_2$ system appears to be faster than the C$_0$—PCy$_3$ system under these conditions. The C$_0$—PCy$_3$ system shows similar rates under both the CD$_2$Cl$_2$ and 90% ketone conditions. However, it appears that the C$_0$—PCy$_3$ catalyst dies much slower in the absence of the halogenated solvents. As was the case for the hydrogenations in CD$_2$Cl$_2$, the Mo—C$_3$—PPh$_2$ catalyst is substantially better than its Mo—C$_2$—PPh$_2$ analog. The hydrogenation rates appear to slow down less rapidly overall. A number of reactions rates appear to be clearly limited by the H$_2$ concentration since the rate increases after more H$_2$ is added.

Surprisingly, when the catalyst concentration of the C$_2$—PCy$_2$ system was doubled from 30 to 60 mM, the rate of catalysis significantly slowed (the catalytic rate was halved). Reaction solutions at 100° C. did hydrogenate 3-pentanone, but at slower rates. The catalyst also died off much more rapidly at elevated temperatures.

These reactions clearly show that both the Mo—C$_0$—PR$_3$ and Mo—C$_n$—PR$_2$ (n=2 or 3) catalysts can hydrogenate more than 60 equivalents of 3-pentanone. In other words, none of the catalysts died off as rapidly under these conditions. The results indicate that the C$_0$—PR$_3$ catalysts formed under these conditions are as good or better than their bridged analogs. As mentioned above, these reactions were run under a deficiency of hydrogen and, because of this, interpretation of the results is somewhat ambiguous.

Neat Reactions (30 mM Catalyst, at Least 100 mL of H$_2$ at 3.8 atm)

The best catalytic results were achieved using a third set of conditions. The neat reactions (i.e., reactions in which the ketone to be hydrogenated serves as the solvent) were usually run with at least a 1:1 ratio of H$_2$ to substrate. For most reactions, a 3-fold excess of H$_2$ (with respect to 3-pentanone) was present at the initialization of the reaction. The standard reaction conditions were 33 mM catalyst, about 300–1200 equivalents of 3-pentanone, and at least 4.1 atm H$_2$ (the catalyst loading was therefore 0.08–0.34 mole-%). As before, the BAr'$_4$$^-$, BF$_4$$^-$, or PF$_6$$^-$-based catalysts were generated in situ by reaction of HMo(CO)$_2$[η$^5$:η$^1$—C$_5$H$_4$(CH$_2$)$_n$PR$_2$] (n=2 or 3) or HMo(CO)$_2$Cp(PR$_3$) with Ph$_3$C$^+$A$^-$ (A$^-$=BAr'$_4$$^-$, BF$_4$$^-$, or PF$_6$$^-$). The corresponding triflates, Mo(CO)$_2$[η$^5$:η$^1$—C$_5$H$_4$(CH$_2$)$_2$PR$_2$](OTf) (37 and 38, R=Cy or $^t$Bu) or Mo(CO)$_2$Cp(PR$_3$)(OTf) (R=Ph, Cy) were added as isolated materials. These reactions used approximately the same sample volumes (630 μL) as the previous reaction conditions (700 μL). The reactions were run at room temperature, 50° C. and 75° C. Only one or two samples were taken during catalysis in order to minimize sampling effects on the catalytic results. The solutions were always kept under a positive pressure of H$_2$. In most cases, the catalytic system was not greatly perturbed by sampling.

TABLE IV

Neat Hydrogenation of 3-Pentanone by a Series of Mo Catalysts

| Line | Precatalyst | Ligand | anion | T, °C. | Mole % of catalyst‡ | $PH_2$ @ rt (atm) | $H_2$: ket ratio | $TON_{total}$ @ ≈ 10 days ($TON_{ether}$) | t | Max TON | Max % conversion | Max time (days) |
|---|---|---|---|---|---|---|---|---|---|---|---|---|
| 1 | 11 | $C_2$-$PPh_2$ | $BAr'_4$ | 25 | 0.34 | 4.1 | 3.3 | 6 (?) | 9.6 | 21 | 9 | 29.9 |
| 2 | 11 | $C_2$-$PPh_2$ | $BAr'_4$ | 50 | 0.34 | 4.1 | 2.7 | 65 (1) | 9.7 | | | |
| 2A | 11 | $C_2$-$PPh_2$ | $BAr'_4$ | 50 | 0.34 | 4.1 | — | — | — | 92 | 31 | 30.1 |
| 3 | 11 | $C_2$-$PPh_2$ | $BAr'_4$ | 75 | 0.16 | 4.1 | 1.6 | 92 (8) | 10.2 | 92 | 31 | 28.9 |
| 4 | 26 | $C_3$-$PPh_2$ | $BAr'_4$ | 25 | 0.34 | 4.1 | 3.3 | — | — | 16 | 5 | 30.7 |
| 5 | 26 | $C_3$-$PPh_2$ | $BAr'_4$ | 50 | 0.34 | 4.1 | 3.3 | — | — | 110 | 37 | 30.7 |
| 6 | 26 | $C_3$-$PPh_2$ | $BAr'_4$ | 75 | 0.16 | 4.1 | 1.6 | 93 (11) | 9.8 | 94 | 15 | 29.8 |
| 7 | 12 | $C_2$-$PCy_2$ | $BAr'_4$ | 25 | 0.34 | 4.1 | 3.3 | 24 (?) | 9.6 | 62 | 21 | 29.9 |
| 8 | 12 | $C_2$-$PCy_2$ | $BAr'_4$ | 50 | 0.34 | 4.1 | 3.3 | 139 (11) | 9.6 | 183 | 62 | 29.9 |
| 9 | 12 | $C_2$-$PCy_2$ | $BAr'_4$ | 50 | 0.11 | 4.1 | 1.1 | 129 (9) | 9.9 | 186 | 29 | 30.0 |
| 10 | 12 | $C_2$-$PCy_2$ | $BAr'_4$ | 50 | 0.34 | 55.8 | 12.1 | 297 (34) | 8.0 | 297 | 100 | 8.0 |
| 11 | 12 | $C_2$-$PCy_2$ | $BF_4$ | 50 | 0.34 | 4.1 | 3.3 | 104 (6) | 9.9 | 144 | 49 | 30.0 |
| 12 | 12 | $C_2$-$PCy_2$ | $PF_6$ | 50 | 0.34 | 4.1 | 3.3 | 82 (2) | 9.8 | 131 | 44 | 29.8 |
| 13 | 37 | $C_2$-$PCy_2$ | OTf | 50 | 0.34 | 4.1 | 3.3 | 126 (4) | 9.8 | 223 | 75 | 29.9 |
| 14 | 12 | $C_2$-$PCy_2$ | $BAr'_4$ | 75 | 0.16 | 4.1 | 1.6 | 148 (10) | 9.7 | 217 | 35 | 29.7 |
| 15 | 12 | $C_2$-$PCy_2$ | $BF_4$ | 75 | 0.16 | 4.1 | 1.6 | 78 (4) | 10.2 | 107 | 17 | 28.9 |
| 16 | 37 | $C_2$-$PCy_2$ | OTf | 75 | 0.16 | 4.1 | 1.6 | 408 (39) | 10.2 | 507 | 83 | 28.9 |
| 17 | 37 | $C_2$-$PCy_2$ | OTf | 75 | 0.08 | 4.1 | 0.81 | 486 (17) | 10.0 | 654 | 53 | 32.0 |
| 18 | 37 | $C_2$-$PCy_2$ | OTf | 75 | 0.08 | 54.4 | 8.6 | 507 (32) | 10.7 | 507 | 41 | 10.7 |
| 19 | 13 | $C_2$-$P^tBu_2$ | $BAr'_4$ | 25 | 0.34 | 4.1 | 3.3 | 48 (3) | 9.8 | 52 | 18 | 29.9 |
| 20 | 13 | $C_2$-$P^tBu_2$ | $BAr'_4$ | 50 | 0.34 | 4.1 | 3.3 | 86 (6) | 9.8 | | | |
| 20A | 13 | $C_2$-$P^tBu_2$ | $BAr'_4$ | 50 | 0.34 | 4.1 | — | — | — | 118 | 40 | 30.1 |
| 21 | 13 | $C_2$-$P^tBu_2$ | $BAr'_4$ | 75 | 0.16 | 4.1 | 1.6 | 68 (4) | 10.2 | 85 | 14 | 28.9 |
| 22 | 38 | $C_2$-$P^tBu_2$ | OTf | 75 | 0.16 | 4.1 | 1.6 | 47 (4) | 10.0 | 61 | 10 | 32.0 |
| 23 | $HMo(CO)_2CpPCy_3$ | $C_0$-$PCy_3$ | $BAr'_4$ | 25 | 0.34 | 4.1 | 2.7 | 39 (2) | 9.7 | | | |
| 23A | $HMo(CO)_2CpPCy_3$ | $C_0$-$PCy_3$ | $BAr'_4$ | 25 | 0.34 | 4.1 | — | — | — | 53 | 18 | 30.1 |
| 24 | $HMo(CO)_2CpPCy_3$ | $C_0$-$PCy_3$ | $BAr'_4$ | 50 | 0.34 | 4.1 | 3.3 | 76 (7) | 9.9 | 117 | 39 | 30.7 |
| 25 | $HMo(CO)_2CpPCy_3$ | $C_0$-$PCy_3$ | $PF_6$ | 50 | 0.34 | 4.1 | 3.3 | 14 (0.3) | 9.8 | 20 | 7 | 29.8 |
| 26 | $HMo(CO)_2CpPCy_3$ | $C_0$-$PCy_3$ | $BF_4$ | 50 | 0.34 | 4.1 | 3.3 | 20 (?) | 9.9 | 23 | 8 | 29.9 |
| 27 | $[Mo(CO)_2CpPCy_3OTf]$ | $C_0$-$PCy_3$ | OTf | 50 | 0.16 | 4.1 | 3.3 | 8 (0.2) | 10.1 | 14 | 2 | 32.1 |
| 28 | $HMo(CO)_2CpPCy_3$ | $C_0$-$PCy_3$ | $BAr'_4$ | 75 | 0.16 | 4.1 | 1.6 | 58 (4) | 10.2 | 60 | 10 | 28.9 |
| 29 | $[Mo(CO)_2CpPCy_3OTf]$ | $C_0$-$PCy_3$ | OTf | 75 | 0.16 | 4.1 | 1.6 | 19 (1) | 10.0 | 23 | 4 | 32.1 |
| 30 | $]Mo(CO)_2CpPPh_3OTf]$ | $C_0$-$PPh_3$ | OTf | 75 | 0.16 | 4.1 | 1.6 | 6 (?) | 10.1 | 14 | 2 | 20.9 |

‡0.08 mole-% corresponds to 1226 equivalents 3-pentanone, 0.11 mole-% corresponds to 891 equivalents 3-pentanone, 0.16 mole-% corresponds to 613 equivalents 3-pentanone, and 0.34 mole-% corresponds to 297 equivalents 3-pentanone.

Results for the neat hydrogenations of 3-pentanone are summarized in Table IV. The neat reaction conditions resulted in catalytic rates up to ten times better than those observed for the previous reaction conditions (this is based on a rough comparison of the best results for all three reaction conditions at 10 days of reactions). One of the most promising results was found for the Mo—$C_2$—$PCy_2$—OTf catalyst system run under 0.16 mole percent catalyst (613 equivalents 3-pentanone) at 75° C. (line 16). The reaction went to 83% conversion, with 507 total turnovers after about 30 days. Reactions run under lower catalyst loading (0.08 mole %, 1226 equivalents 3-pentanone, line 17) gave the highest total turnovers (654), although the reaction had gone to only 53% conversion after 32 days. Based on previous results (where $BAr'_4$ counterion was needed to produce an active catalyst), it was surprising that the OTf species was the best catalyst. The related Mo—$C_2$—$PCy_2$—$BAr'_4$ system was only one-third as active, giving 217 TON (Total) (35% conversion, line 14) after 30 days at 75° C. at a catalyst loading of 0.16 mole-%. A number of the other catalysts, in particular the Mo—$C_0$—$PCy_3$—$BAr'_4$ (line 24) and Mo—$C_2$—$P^tBu_2$—$BAr'_4$ (line 20) and Mo—$C_3$—$PPh_2$—$BAr'_4$ (line 5) systems are fairly active at 50° C., giving percent-conversions of 39%, 40% and 37% (about 110–120 turnovers) at 0.34 mole-% catalyst concentration. These results are, however, not as good as those seen for the Mo—$C_2$—$PCy_2$—OTf (line 13, 75% conversion, 223 TON) and Mo—$C_2$—$PCy_2$—$BAr'4$ (line 8, 62% conversion, 183 TON) systems under the same conditions (50° C., 0.34 mole-% catalyst). The Mo—$C_2$—$PPh_2$—$BAr'_4$ system (line 2A) gave a moderate %-conversion (31%, 92 TON) at 50° C. and a catalyst loading of 0.34%.

The results in Table IV indicate that the reaction rates are strongly dependent on temperature. In all cases, the room temperature reactions are quite slow. For example, the Mo—$C_2$—$PCy_2$—$BAr'_4$ system's hydrogenation rate is almost tripled when the reaction is run at 50° C. (line 8, 62% conversion) versus room temperature (line 7, 21% conversion) after 30 days of reaction. Similar improvements of reactivity are observed for the Mo—$C_2$—$PPh_2$—$BAr'_4$ (line 1 vs. line 2A), Mo—$C_2$—$P^tBu_2$—$BAr'_4$ (line 19 vs. line 20A), and Mo—$C_0$—$PCy_3$—$BAr'_4$ (line 23A vs. line 24) systems. The effect is even more striking in the Mo—$C_3$—$PPh_2$—$BAr'_4$ system, where the percent-conversion at 50° C. (line 5, 37% conversion) is approximately 7 times better than that at room temperature (line 4, 5% conversion) after 30 days. While an increase from room temperature to 50° C. improved the hydrogenation rate for all catalysts, a further increase to 75° C. was not always beneficial.

In the case of the $C_2$-bridged Mo—$PPh_2$ systems, the rates of hydrogenation at 10 days of reaction at 75° C. (lines 3) show significant improvement when compared to the same reactions at 50° C. (lines 2). Unfortunately, after 30 days of reaction, it is clear that this catalyst was inactive, as no further turnovers occur. Thus the initial rates may be very high, but the thermal stability of the catalysts is low. In the case of the Mo—$C_2$—$P^tBu_2$—$BAr'_4$ system, the reaction at 75° C. results in lower % conversions than observed for 50° C. (lines 21 vs. 20). In all cases, including the very successful Mo—$C_2$—$PCy_2$—$A^-$ systems, the solutions turn from redish to a dark brown after prolonged reaction at 75° C. Observations showed that the Mo—$C_2$—$PCy_2$—$BAr'_4$ and Mo—$C_2$—$PCy_2$—OTf systems are both more reactive and more stable at higher temperature (even though they also turn brown over time).

The test results show that the choice of counterions for this reaction is quite important. For all catalytic systems except, the Mo—$C_2$—$PCy_2$ system, the bulky, noncoordinating $BAr'_4$ anion is required in order to observe significant hydrogenation. For example, substituting the $BAr'_4$ anion with $PF_6^-$, $BF_4^-$ or $OTf^-$ anions in the Mo—$C_0$—$PCy_3$ system results in essentially catalytically inactive systems (lines 25–27 and line 29), regardless of temperature. Likewise, the Mo—$C_0$—$PCy_3$—OTf and Mo—$C_0$—$PPh_3$—OTf systems exhibit low activity at 75° C. (lines 27, 29 and 30), regardless of temperature (note that solutions of these catalysts rapidly decompose as evidenced by the precipitation of a fine black solid, presumably $Mo^0$, during the reaction). The Mo—$C_2$—$P^tBu_2$—OTf system is somewhat active at 75° C. (61 TON, 10% conversion at 30 days, line 22), although the analogous $BAr'_4$ catalyst is more active at this temperature (85 TON, 14% conversion at 30 days line 21). The Mo—$C_2$—$PCy_2$ appears to be active, regardless of counterion. The $OTf^-$ analog of these catalysts is more active than the $BAr'_4$ system (223 TON, 75% conversion at 50° C. for 30 days, line 13 vs. 170 TON, 62% conversion at 50° C. for 30 days, 8 respectively). The $BF_4^-$ and $PF_6^-$ analogs of this system are also active catalysts at 50° C. for 30 days, although their activity is somewhat lower (144 TON, 49% conversion, line 11, and 133 TON, 44% conversion, line 12, respectively) than that observed for the $BAr'_4^-$ system.

The particular activity of the OTf system is still not fully understood, although it may be related to the OTf-group's ability to stabilize the catalytic intermediates. Clearly the Mo—$C_2$—$PCy_2$ system is superior to its non-bridged analog (Mo—$C_0$—$PCy_3$), regardless of anion. The Mo—$C_2$—$PCy_2$—OTf system is also substantially more cost effective in comparison to the analogous Mo—$C_2$—$PCy_2$—$BAr'_4$ system. This is likely due to the stabilizing effect of the bridge. The nonbridged catalytic systems are, as expected, quite unstable due to the ease with which the phosphine can disassociate from the metal (leading to catalyst death). This is clearly shown in the results listed in Table IV.

EXAMPLES

For the examples disclosed herein, the terms used to describe the results are defined as follows. Turnovers are number of moles of ketone hydrogenated per mole of catalyst. Total turnover number [TON (total)] includes the alcohol (3-pentanol) formed by hydrogenation of the ketone, plus the ether $(Et_2CH)_2O$ formed through condensation of two molar equivalents of the alcohol. Each equivalent of ether is counted as representing two hydrogenation equivalents (or turnovers of the catalyst), since it takes two alcohols to form one ether.

Example 1

For this example, $HMo(CO)_2[\eta^5:\eta^1—C_5H_4(CH_2)_nPCy_2]$ (9.3 mg, $2.1\times10^{-5}$ mol) and $Ph_3C^+BAr'_4^-$ (23.2 mg, $2.1\times10^{-5}$ mol; 1 equiv) were placed in a glass vial in a glove box, and 3-pentanone (630 μL, 537 mg, 6.24 mmol, 297 equiv) was added. After the solids had dissolved, the solution was transferred to a glass tube (125 mL capacity) equipped with a teflon valve. The tube was sealed in the drybox under argon and connected to a vacuum line. The solution was freeze-pump-thawed two times. The sample was frozen a third time and the tube was submersed in liquid nitrogen. The tube was then filled with about 1.1 atm $H_2$, sealed, and warmed to room temperature. The resulting tube contained about 4.1 atm $H_2$ (125 mL at 4.1 atm, 20.1 mmol, 1000 equiv.) at room temperature.

The reaction was carried out at 50° C. in a constant-temperature bath. Aliquots were removed by cooling the tube to 77° K and opening to 1 atm $H_2$. The tube was warmed to room temperature, and the aliquot (about 60 μL) was removed for analysis. After removal of the aliquot, the tube was again cooled to 77° K and evacuated, then filled with 1.1 atmospheres $H_2$ at 77° K and re-sealed. The aliquot was diluted in $CD_2Cl_2$ (500 μL) and the solution was analyzed by $^1H$ NMR. After 9.6 days, TON (total)=139, of which TON (ether) was 11. After 19.8 days, TON (total)= 164, of which TON (ether) was 12. After 29.9 days, TON (total)=183, of which TON (ether) was 13, representing a total of 62% conversion of the initial ketone.

Example 2

This example is similar to Example 1 above, except that $BF_4^-$ was used as the counterion. $HMo(CO)_2[\eta^5:\eta^1—C_5H_4(CH_2)_nPCy_2]$ (9.3 mg, $2.1\times10^{-5}$ mol) and $Ph_3C^+BF_4^-$ (6.9 mg, $2.1\times10^{-5}$ mol; 1 equiv) were placed in a glass vial in a glove box, and 3-pentanone (630 μL, 537 mg, 6.24 mmol, 297 equiv) was added. The reaction was carried out at 50° C., and the same procedure described for Example 1 was followed. After 9.6 days, TON (total)=104, of which TON (ether) was 6. After 20.9 days, TON (total)=133, of which TON (ether) was 5. After 30.0 days, TON (total)=144, of which TON (ether) was 9, representing a total of 48% conversion of the initial ketone.

Example 3

This example is similar to Examples 1 and 2 above, except that the counterion was $PF_6^-$. $HMo(CO)_2[\eta^5:\eta^1—C_5H_4(CH_2)_nPCy2]$ (9.3 mg, $2.1\times10^{-5}$ mol) and $Ph_3C^+ PF_6^-$ (8.2 mg, $2.1\times10^{-5}$ mol; 1 equiv) were placed in a glass vial in a glove box, and 3-pentanone (630 μL, 537 mg, 6.24 mmol, 297 equiv) was added. The reaction was carried out at 50° C., and the same procedure described for Example 1 was followed. After 9.8 days, TON (total)=82, of which TON (ether) was 2. After 19.9 days, TON (total)=111, of which TON (ether) was 6. After 29.8 days, TON (total)=131, representing a total of 44% conversion of the initial ketone.

Example 4

For this example, $HMo(CO)_2[\eta^5:\eta^1—C_5H_4(CH_2)_nPCy_2]$ OTf (12.4 mg, $2.1\times10^{-5}$ mol) was placed in a glass vial in a glove box, and 3-pentanone (630 μL, 537 mg, 6.24 mmol, 297 equiv) was added. The reaction was carried out at 50° C., and the same procedure described for Example 1 was followed. After 9.8 days, TON (total)=126, of which TON (ether) was 4. After 19.8 days, TON (total)=188, of which TON (ether) was 9. After 29.9 days, TON (total)=223, of which TON (ether) was 13, representing a total of 75% conversion of the initial ketone.

Example 5

This example is similar to Example 1, except that it is carried out at high pressure of $H_2$. $HMo(CO)_2[\eta^5:\eta^1—C_5H_4$ (CH$_2$)$_n$PCy$_2$] (27.9 mg, 6.3×10$^{-5}$ mol) and Ph$_3$C$^+$BAr'$_4$$^-$ (69.6 mg, 6.3×10$^{-5}$ mol; 1 equiv) were placed in a stainless steel high pressure vessel in a glove box, and 3-pentanone (1.9 mL, 18.8 mmol, 298 equiv) was added. The vessel was sealed and removed from the glovebox. H$_2$ was added at 820 psi (at room temperature), and the reaction was carried out at 50° C. Prior to removal of each sample for analysis, the reaction was cooled to room temperature, and the pressure was slowly vented.

The sample for NMR analysis was removed in a drybox under an argon atmosphere, and the vessel was resealed and re-pressurized with H$_2$. After 24 hours, the reaction was 50% complete; TON (total)=148, of which TON (ether) was 12. After 3.0 days, the reaction was 94% complete; TON (total)=257, of which TON (ether) was 22. After 5.0 days, TON (total)=296, of which TON (ether) was 38, representing a total of 99.5% conversion of the initial ketone.

Example 6

For this example, HMo(CO)$_2$[η$^5$:η$^1$—C$_5$H$_4$(CH$_2$)$_2$P$^t$Bu$_2$] (8.2 mg, 2.1×10$^{-5}$ mol) and Ph$_3$C$^+$BAr'$_4$$^-$ (23.2 mg, 2.1×10$^{-5}$ mol; 1 equiv) were placed in a glass vial in a glove box, and 3-pentanone (630 μL, 537 mg, 6.24 mmol, 297 equiv) was added. The reaction was carried out at 23° C., and the same procedure described for Example 1 was followed. After 9.8 days, TON (total)=49, of which TON (ether) was 2. After 19.8 days, TON (total)=53, of which TON (ether) was 4. After 29.9 days, TON (total)=55, of which TON (ether) was 5, representing a total of 18% conversion of the initial ketone.

Example 7

In this example, HMo(CO)$_2$[η$^5$:η$^1$—C$_5$H$_4$(CH$_2$)$_n$PCy$_2$] OTf (12.4 mg, 2.1×10$^{-5}$ mol) was placed in a glass vial in a glove box, and 3-pentanone (1.2 mL, 12.9 mmol, 613 equiv) was added. The reaction was carried out at 75° C., and the same procedure described for Example 1 was followed. After 10.2 days, TON (total)=408, of which TON (ether) was 39. After 20.3 days, TON (total)=474, of which TON (ether) was 22. After 28.9 days, TON (total)=507, of which TON (ether) was 23, representing a total of 83% conversion of the initial ketone.

Example 8

This example is similar to several examples above, except that the C$_3$ bridged complex was used, instead of a C$_2$ bridged complex. HMo(CO)$_2$[η$^5$:η$^1$—C$_5$H$_4$(CH$_2$)$_n$PPh$_2$] (9.3 mg, 2.1×10$^{-5}$ mol) and Ph$_3$C$^+$BAr'$_4$$^-$ (23.2 mg, 2.1×10$^{-5}$ mol; 1 equ) were placed in a glass vial in a glove box, and 3-pentanone (630 μL, 537 mg, 6.24 mmol, 297 equiv) was added. The reaction was carried out at 50° C., and the same procedure described for Example 1 was followed. After 19.9 days, TON (total)=92, of which TON (ether) was 12. After 30.7 days, TON (total)=110, of which TON (ether) was 13.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

What is claimed is:

1. A catalyst for the hydrogenation of an organic compound which contains at least one reducible functional group selected from the group consisting of R*(C=O)R' and R*(C=O)H, wherein R* and R' are selected from hydrogen (H) or any alkyl or aryl group, said catalyst comprising a metal hydride represented by the formula:

wherein M represents a molybdenum atom or a tungsten atom; X is a carbon atom, a silicon atom or a combination of carbon (C) and silicon (Si) atoms; n is any positive integer; R represents two hydrocarbon groups selected from H, an aryl group and an alkyl group, and wherein both R groups can be the same or different.

2. A catalyst according to claim 1, wherein said catalyst is prepared by reacting said metal hydride with Ph$_3$C$^+$A$^-$, and wherein A$^-$ represents an anion.

3. A catalyst according to claim 2, wherein said anion (A$^-$) is selected from the group consisting of BF$_4$$^-$, PF$_6$$^-$, CF$_3$SO$_3$$^-$ and BAr'$_4$$^-$, wherein Ar'=3,5-bis(trifluoromethyl) phenyl.

4. A catalyst according to claim 2, wherein said metal hydride is reacted with said Ph$_3$C$^+$A$^-$ either before reacting with said organic compound or in the reaction mixture with said organic compound.

5. A catalyst according to claim 1, wherein said catalyst is prepared by reacting said metal hydride with Ph$_3$C$^+$A$^-$ in said reaction mixture and wherein said anion (A$^-$) is selected from the group consisting of BF$_4$$^-$, PF$_6$$^-$, and BAr'$_4$$^-$, wherein Ar'=3,5-bis(trifluoromethyl)phenyl.

6. A catalyst according to claim 1, wherein said catalyst is prepared by reacting said metal hydride with Ph$_3$C$^+$A$^-$ prior to reacting with said organic compound and wherein said anion (A$^-$) is CF$_3$SO$_3$$^-$.

7. A catalyst according to claim 1, wherein a bridge of carbon and/or silicon groups connect the cyclopentadienyl ligand (—C$_5$H$_4$) to the phosphine ligand (PR$_2$) of said metal hydride, and wherein n is an integer from 1 to 6.

8. A catalyst according to claim 2, wherein a bridge of carbon and/or silicon groups connect the cyclopentadienyl ligand (—C$_5$H$_4$) to the phosphine ligand (PR$_2$) of said metal hydride.

9. A catalyst according to claim 2, wherein R is a cyclohexyl group (C$_6$H$_{11}$), a methyl group (CH$_3$), a phenyl group (C$_6$H$_5$) or a tert-butyl ($^t$Bu) system.

* * * * *